United States Patent [19]

Falk et al.

[11] Patent Number: 5,091,550
[45] Date of Patent: Feb. 25, 1992

[54] 5,5-BIS (PERFLUOROALKYLHETEROMETHYL)-2-HYDROXY-2-OXO-1,3,2-DIOXAPHOSPHORINANES, DERIVED ACYCLIC PHOSPHORUS ACIDS AND SALTS OR ESTERS THEREOF

[75] Inventors: Robert A. Falk, New City, N.Y.; Kirtland P. Clark, Bethel, Conn.

[73] Assignee: Ciba-Geigy Corporation, Ardsley, N.Y.

[21] Appl. No.: 513,356

[22] Filed: Apr. 20, 1990

[51] Int. Cl.$^5$ .......................... C07F 9/09; C07F 9/141
[52] U.S. Cl. ................................. 558/165; 558/158; 558/159; 558/164; 558/169; 558/170; 558/175; 558/184; 558/186
[58] Field of Search ............... 558/165, 184, 186, 158, 558/159, 170, 175, 169

[56] References Cited

U.S. PATENT DOCUMENTS 3,899,484 8/1975 Walter .............................. 558/186

Primary Examiner—Mary C. Lee
Assistant Examiner—Michael G. Ambrose
Attorney, Agent, or Firm—Edward McC. Roberts

[57] ABSTRACT

5,5-Bis(perfluoroalkylheteromethyl)-2-hydroxy-2-oxo-1,3,2-dioxaphosphorinanes, derived acyclic phosphorus and phosphoric acids obtained by ring-opening, and salts or esters thereof are prepared from heteroatom containing perfluoroalkyl terminated neopentyl glycols of the formula: $HO[CH_2C(CH_2-X-E_n-R_f)_2CH_2O]H$ by cyclization with appropriate phosphorus containing esters or acids, or hydrolysis. These compositions provide improved thermal stability, and useful low surface energy oil and water repellent coatings for textiles, glass, paper, leather and other materials.

Another aspect of this invention relates to the use of the phosphite group containing products as polymer stabilizers.

16 Claims, No Drawings

5,5-BIS(PERFLUOROALKYLHETEROMETHYL)-2-HYDROXY-2-OXO-1,3,2-DIOXAPHOSPHORINANES, DERIVED ACYCLIC PHOSPHORUS ACIDS AND SALTS OR ESTERS THEREOF

BACKGROUND OF THE INVENTION

This invention relates to 5,5-bis(perfluoroalkylheteromethyl)-2-hydroxy-2-oxo-1,3,2-dioxaphosphorinanes, derived acyclic phosphorus and phosphoric acids obtained by ring-opening an salts or esters thereof.

Bis-perfluoroalkyl substituted phosphorinanes, derived acyclic phosphorus and phosphoric acids, and salts or esters thereof are not reported. The subject bis-perfluoroalkyl phosphorus derivatives are readily isolated in high yield and purity. They have a low free surface energy that provides oil and water repellency to a wide variety of substrates. Their primary use is to impart oil and water repellency to textiles, glass, paper, leather, and other compositions.

Another aspect of this invention relates to the use of the phosphite group containing products as polymer stabilizers. Prior art bis-perfluoroalkyl group containing phosphates are described in U.S. Pat. Nos. 3,083,224, 3,094,547, 3,412,181, 3,492,374 and 3,812,217, 3,919,361, and in EP 288,933 as useful for textile treating or grease and oil repellents for paper.

DETAILED DISCLOSURE

This invention relates to a method of making 5,5-bis(perfluoroalkylheteromethyl)-2-hydroxy-2-oxo-1,3,2-dioxaphosphorinanes, derived acyclic phosphoric and phosphorus acids obtained by ring-opening, and salts or esters thereof.

This invention relates to the use of said reaction products as coatings on paper, textiles, glass, linoleum, leather, wood, tile, metals, plastics, and particularly on paper.

Also, the invention provides a method for treating these materials to impart oil and water repellency thereto. The use of the described fluorochemicals provides thermally stable materials that are oil and water repellent at lower application levels than are provided by previously used treating compositions.

Another aspect of this invention relates to the use of the phosphite group containing products as polymer stabilizers.

This invention also relates to a substrate containing 0.01 to 10% by weight of a fluorine-containing composition, at least part of said fluorine provided by one or more units derived from the subject $R_f$-chemicals.

The novel heteroatom containing $R_f$-neopentyl phosphorus derivatives have the general formulas I, Ia and Ib for phosphates and II, IIa and IIb for phosphites.

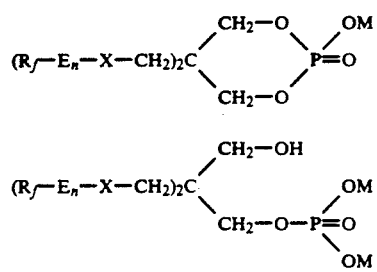

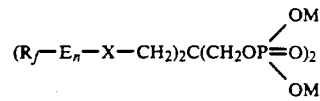

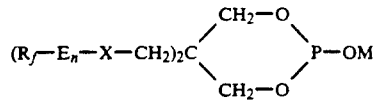

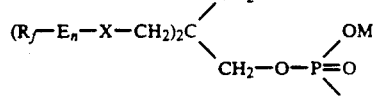

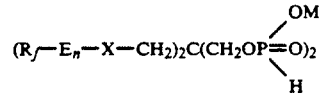

wherein $R_f$ is a straight or branched chain perfluoroalkyl of 2 to 12 carbon atoms or perfluoroalkyl of 2 to 6 carbon atoms substituted by perfluoroalkoxy of 2 to 6 carbon atoms, n=1 or 0, and when n=1, E is a branched or straight chain alkylene of 2 to 10 carbon atoms or said alkylene interrupted by one to three groups selected from the group consisting of —NR—, —O—, —S—, SO$_2$—, —COO—, —OOC—, —CONR—, —NRCO—, —SO$_2$NR—, and —NRSO$_2$—, or terminated at the $R_f$ end with —CONR— or —SO$_2$NR—, where $R_f$ is attached to the carbon or sulfur atom, and X is —S—, —O—, —SO$_2$—, or —NR—, and when n=O, X is a direct bond, —CONR— or —SO$_2$NR—, where $R_f$ is attached to the carbon or sulfur atom and where R is independently hydrogen, alkyl of 1 to 6 carbon atoms or hydroxyalkyl of 2 to 6 carbon atoms, and M is independently hydrogen, lower alkyl, an alkyl- or mixed polyalkyl- substituted aromatic group, or represents an ammonium, organo-ammonium, alkali metal or alkaline earth metal salt of the respective phosphite or phosphate group.

It is understood that the $R_f$ group usually represents a mixture of perfluoroalkyl moieties. When the $R_f$ group is identified as having a certain number of carbon atoms, said $R_f$ group also usually concomitantly contains a small fraction of perfluoroalkyl groups with a lower number of carbon atoms and a small fraction of perfluoroalkyl groups with a higher number of carbon atoms. Commonly, the perfluoroalkyl group is preferably a mixture of C$_4$F$_9$—, C$_6$F$_{13}$—, C$_8$F$_{17}$—, C$_{10}$F$_{21}$—, C$_{12}$F$_{25}$— and C$_{14}$F$_{29}$—.

Preferably the instant compounds are those where $R_f$ is perfluoroalkyl of 2 to 12 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$—, —CH$_2$CH$_2$OCH$_2$CH$_2$—, or —SO$_2$NHCH$_2$CH$_2$—, and X is —S—, —SO$_2$— or —O—.

5,5-Bis(perfluoroalkylheteromethyl)-2-hydroxy(-2-oxo)-1,3,2-dioxaphosphorinanes of formulas I and II, and salts or esters thereof are obtained directly from heteroatom containing perfluoroalkyl terminated neopentyl glycols described in U.S. patent application Ser. No. 339,326.

One or more perfluoroalkyl substituents can be substituted at other positions of the stable 1,3,2-dioxyphosphorinane ring to prepare analogous phosphates and phosphites. These products can be hydrolyzed to acyclic derivatives.

However, the 5,5-bis(perfluoroalkylheteromethyl) substituents cited herein are most accessible.

Phosphates of type (I) are obtained by reaction with polyphosphoric acid, phosphoric acid, or esters thereof. Alternately, they are obtained indirectly by first cyclizing the glycols with POCl$_3$ or PCl$_5$, followed by reaction with water or hydroxylic reactant.

Phosphites of type (II) are obtained by reaction with phosphorus acid or phosphite esters. They may be obtained indirectly by first cyclizing the glycols with PCl$_3$, followed by reaction with water, or hydroxylic reactant.

Derived acyclic acids of types (Ia), 2,2-bis(1,1,2,2-tetrahydroperfluoroalkylheteromethyl)-3-hydroxy-1-propyl phosphoric acid, and (IIa), 2,2-bis(1,1,2,2-tetrahydroperfluoroalkylheteromethyl)-3-hydroxy-1-propyl phosphorus acid, and salts or esters thereof, may be obtained by hydrolysis of the respective 1,3,2-dioxaphosphorinanes. Small quantities of compounds of type (Ib) or (IIb) are usually present.

Phosphites of types (II), (IIa), and (IIb) can be converted to phosphates of types (I), (Ia), and (Ib) by conventional oxidation.

Most preferred are those compounds where R$_f$ is perfluoroalkyl of 6 to 12 carbon atoms, E is ethylene, and X is S, i.e.,

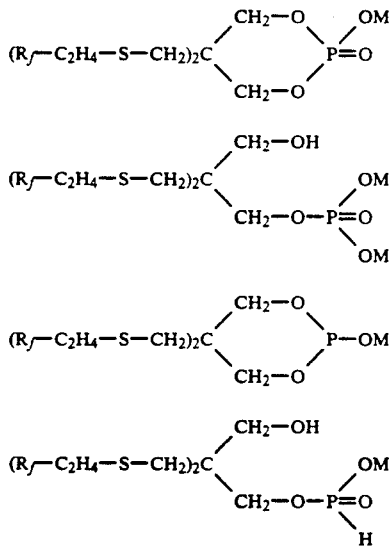

In one preferred embodiment the starting material is:

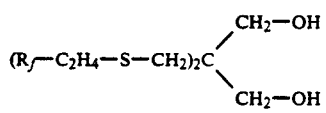

The bis-sulfido-reactants or resulting phosphorus containing products can be readily oxidized to the corresponding bis-sulfones by peracetic acid (H$_2$O$_2$/acetic acid) or by other conventional oxidants. Temperatures of 30°–100° C. are appropriate, and an excess of the oxidizing agent ensures that the intermediate sulfoxides are completely oxidized.

These compounds have very low free surface energies and therefore, have oil and water repellent properties, and mold release and other properties associated with low free surface energy. It should be noted that the compounds of this invention are Characterized by the presence of two perfluoroalkylhetero groups in close proximity a characteristic that provides improved oil and water repellent properties over the fluorinated compositions of the prior art. Further, the two perfluoroalkylthio groups connect via a neopentyl moiety that does not permit the thermal elimination of mercaptan by beta-elimination. Hence, these R$_f$-phosphorus derivatives have enhanced thermal stability.

It is an object of the present invention to minimize by-products in the ammonium and amine salts of the present invention by reacting the corresponding bis-perfluoroalkyl group containing acids with ammonia or an amine in a diluent substantially inert to the acid and ammonia or amine reactants.

The reaction is neutralized at temperatures between 0° C. and 100° C., preferably at ambient temperature conditions. Where the amine is introduced in gaseous forms, such as anhydrous ammonia or methylamine it can be bubbled through the acid in the liquid diluent medium. As the reaction tends to be exothermic, cooling of the reaction vessel may be advantageously employed. Where the inert diluent is organic in nature, such as a lower alkanol, for example methanol, diethylene glycol dimethyl ether or the like, the ammonium or amine salts reaction product can be recovered by precipitation, or evaporation of the diluent. The ammonium or amine salt does not have to be separated from the solvent media.

The amines should be water soluble mono- or polyamines having a water solubility of at least 2% by weight. Suitable amines are aminomethane, aminoethane 1-aminopropane 2-aminopropane, 1-aminobutane, 1-amino-2-methylpropane, 1,1-dimethylethylamine, 1-aminopentane, isoamylamine, tert-amylamine, allylamine, dimethylamine, diethylamine, diisopropylamine, trimethylamine, triethylamine, tri-n-butylamine, ethylenediamine, 1,2-propanediamine, trimethylenediamine, 1,3-diaminobutane, 1,4-diaminobutane, hexamethylene diamine, diethylenetriamine, triethylenetriamine, tetraethylenepentamine, polyethyleneimine having an average of about 20, 80, 120 or 200 units, diethylaminopropylamine, ethanolamine, diethanolamine, triethanolamine, ethylenediaminetetraacetic acid, nitrilotrisacetic acid, N-(hydroxyethyl)ethylenediamine, N,N'-bis-(hydroxyethyl)- diethylenetriamine, N,N,N',N'-tetrakis-(2-hydroxy-propyl)ethylenediamine, N-(2-hydroxypropyl)ethylenediamine, cyclohexylamine, dicyclohexylamine, and

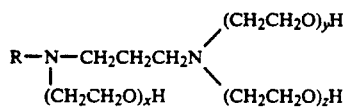

where R is tallow fatty alkyl and x+y+z is 3, 10 or 15, fatty diethanolamines, mono-, di-, and tri-isopropanolamines, or polyoxyethyleneamines.

Preferably the amine is an alkanolamine.

Alternately, quaternary ammonium salts can be obtained from tetraalkylammonium bases by neutralization.

The subject bis-perfluoroalkyl terminated carboxylic acids can be used in-situ by the addition as the free acid to a basic aqueous application formulation. Alternately, it is prepared as a concentrate containing 5 to 80% by weight of the neutralized phosphate salt, optionally in the presence of excess base. The perfluorochemical is applied from water or from a solvent soluble in water to at least 0.1%.

For topical application, suitable aqueous dilutions advantageously contain 0.01% to 5%, preferably 0.02% to 2%, by weight of the amine salts at use dilution. Conventional adjuvants such as water repellent assistants, bacteriostats, coloring agents, surface conditioners and the like, may be included in an amount between about 0.01% and 10% by weight in the emulsion. Also, sizing agents, where the emulsion is to be used on cellulosic substrates, may be present in the amounts of 0.01% to 10% by weight.

The sizing agent may be a natural sizing agent such as animal glue, asphalt emulsions, wax emulsions, rosins, starches, a semi-synthetic sizing agent such as a fatty acid salt or complex a fortified rosin, e.g., trisodium maleoprimaric acid salt sodium alginate or sodium carboxymethyl-cellulose., or a synthetic sizing agent such as an alkylketone dimer, alkylsuccinic anhydrides, polyvinyl alcohol, styrene-maleic anhydride polymers, and the like. Also, mixtures thereof may be used, or an emulsifier may be optionally present in an amount of between about 0.001% to 3% by weight.

Thus, suitable dilutions for topical application contain the following:
(a) 0.01 to 5% by weight of the amine salt;
(b) 0 to 3% by weight emulsifier;
(c) 0 to 5% water repellent assistant, filler, bacteriostat, coloring agent or surface conditioner adjuvant;
(d) 0 to 10% sizing agent, and
(e) the remainder water.

These formulations apply to the surface of the cellulosic, natural or synthetic material by conventional techniques, including padding, spraying, coating, washing, and brushing. After application, the treated surface is dried, with or without an intermediate washing stage. The resulting surface becomes water and oil resistant.

For use as a sizing agent to obtain oil and water repellency, the dilution of the instant aqueous formulations advantageously contains from about 0.0005 to 0.2% by weight of the instant amine salts. The formulations for dilution may be prepared as a concentrate containing between 5% and 80% by weight, preferably 30 to 80% by weight of the amine salt.

Using the $R_f$-compounds and compositions described herein it is possible to prepare fluorochemical emulsions to treat textiles and provide outstanding oil and water-repellent characteristics thereto.

Suitable cellulosic and natural substrates for topical application include paper, non-woven fabrics, textiles, paperboard, wood, wood fiber products such as plywood, hair, including wool, hides, leather, and feathers. Synthetic substrates include nylon fibers and textiles.

While the instant formulations are suitable for rendering a variety of materials oil and water repellent, they are particularly advantageous in rendering articles made from paper pulp, such as paper trays, paper plates and analogous paper articles, both oleophobic and hydrophobic.

In order to further increase the efficiency of application, it is conventional to treat the paper pulp with a cationic agent, or retention aid such as an oxidized or cationically modified starch, which is adsorbed by the paper pulp and tends to increase the amount of fluorochemical transferred to the cellulose substrate.

Suitable cationic agents, conventionally used to treat cellulose materials such as paper pulp, include conventional cationic modified starches, such as INTERBOND C, LOK-SIZE 30, CATO 2, CATO 15 and CATO 17 cationic modified aminoplast resins such as KYMENE 557H from Hercules Inc.; cationic polymers such as HYPO WB-4000 with W.R. Grace Inc.

Suitable cationic resins are described in Bates, "Polyamide-Epichlorhydrin Wet Strength Resin, TAPPI, 52, (6) 1969 and in U.S. Pat. Nos. 3,655,506 and 4,299,654.

Jointly with the perfluoroalkyl group containing acid salts of the invention, can be added one or more of wide choice of water proofing sizing agents selected from classes such as alkyl anhydrides, e.g., FIBRON 68; alkyl ketene dimers e.g., AQUAPEL 360 XC or HERCON 40; polyurethane emulsions, e.g., GRAPHSIZE C., acrylic resins, e.g., CARBOSET., stearyl amine surfactants, e.g., ETHOMEEN 18/25 complexed with a fatty acid, e.g., stearic acid; NEOFAT 14, NEOFAT 47 or HYSTRENE 9718. Suitable hydrophobic sizing agents are described by Davis, et al., TAPPI, 39 (1) pp. 21-23 (1956) and in U.S. Pat. Nos. 4,243,481 and 4,279,794.

The amount of adjuvant and sizing agent used for treating paper is of the range specified for topical application, supra. Thus, for internal or external sizing of paper pulp suitable aqueous dilutions contain:
(a) 0.0005 to 0.1% by weight of the instant amine salts;
(b) 0 to 0.05% by weight emulsifier;
(c) 0 to 5% by weight filler, bacteriostat, fungicide, coloring agent, surface conditioner adjuvant, or retention aid;
(d) 0 to 10% sizing agent; and
(e) the remainder water.

The following examples are intended for illustrative purposes only, and are not intended to restrict the scope of the invention in any way. All parts are by weight unless otherwise specified.

SAMPLE PREPARATION AND TESTING

Pad Application of Fluorochemicals on an External Size

Samples of fluorochemicals are diluted to the test application levels with distilled water. The solutions are added to a 4% aqueous solution of paper maker's starch and then applied to unsized paper by padding (paper dipped through starch solution, and passed through single nip rollers). The resulting sheets are dried at ambient conditions for 15 minutes, then 3 minutes at 200° F. in an "Emerson Speed Drier" (heated metal plate with canvas cover).

Internal Size Application and Testing

Six grams of dry pulp are diluted in 289 ml distilled water and thoroughly dispersed in a blender. To this pulp slurry is added a 1% dilution (as is) of the test dispersion in distilled water and mixed in for 5 minutes. Then, 6 ml of a 1% aqueous solution of cooked cationic starch is added and mixed together for an additional 5 minutes. To this, 24 ml of a 50% (on solids) dilution of a water repellent adjuvant is added and mixed in for another 10 minutes. The resulting slurry is diluted with an additional 500 ml of distilled water and mixed again. This mixture is then poured over a 100 mesh wire screen, with a vacuum applied from below, which pulls the water from the pulp mixture to form a sheet on the screen. The wet sheet is removed from the screen and dried between another screen and hard surface at a pressure of approximately 0.4 lb./in$^2$ at 110° C. for 1½ hours. One ml of hot (110° C.) corn oil is placed on the paper and the time noted for penetrations to occur (20 min. max). Similarly, 1 ml of hot (80° C.) water containing 0.5% of TRITON X-165 wetting agent (from Rohm & Haas) placed on the paper is tested. Paper made in the same manner, including the cationic starch and water repellent adjuvant but without a fluorochemical demonstrated an oil kit number of <1, and held the hot corn oil and hot water/TRITON X-165 solution for less than one minute (began to penetrate as soon as applied).

Grease Resistance Test

Creased test papers are placed over a grid sheet imprinted with 100 squares. Five grams of sand are placed in the center of the crease. A mixture of synthetic oil and a dye for visualization is pipetted onto the sand and the samples are maintained at 60° C. for 24 hours. Evaluation is determined by the percentage of the grid that stains.

Another aspect of this invention relates to the use of the phosphite group containing products as polymer stabilizers. They are Very effective in the stabilization of polyolefins, polyesters, styrenics, engineering thermoplastics, PVC, elastomers, and adhesives. They contribute in achieving improved stability during fabrication compounding, and end use.

Another aspect of this invention relates to a substrate containing 0.01 to 10% by weight of a fluorine-containing composition, at least part of said fluorine being provided by one or more units derived from the subject $R_f$-chemicals.

AATCC Oil Test

The AATCC Oil Rating was determined according to Standard Test method 118-1983 of the American Association of Textile Chemists and Colorists. Ratings are given from 0 (minimum) to 8 (maximum). A commonly accepted level of repellency for oil repellent fabrics in the United States is an oil repellency of 4.

All mentioned AATCC Tests are listed in the Technical manual of the American Association of Textile Chemists and Colorists, volume 61, edition 1986.

Stabilizer Testing

The phosphites are commonly added in concentrations between 0.05 and 0.25%. The effectiveness of different stabilizer systems is best assessed by multiple extrusions. The melt flow and Yellowness Index of the extruded material is determined after each pass.

The invention described above is illustrated by the following examples:

Examples 1 to 7 illustrate the preparation of the 5,5-bis(perfluoroalkylheteromethyl)-2-hydroxy-2-oxo-1,3,2-dioxaphosphorinanes, derived acyclic acids, and salts or esters thereof.

Examples 8 to 14 show the wide diversity of related derivatives that can also be prepared.

Examples 15 and 16 show the usefulness of the subject compounds.

Example 1

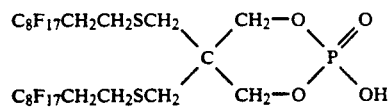

5,5-Bis(1,1,2,2-tetrahydroperfluorodecylthiomethyl)-2-hydroxy-2-oxo-1,3,2-dioxaphosphorinane 2,2-Bis-(1,1,2,2-tetrahydroperfluorodecylthiomethyl)-1,3-propanediol (17.0 g, 0.016 mol) is charged to a three-necked flask with polyphosphoric acid (5.0 g). Ethylene glycol dimethyl ether (7.0 g) is added as solvent, and stirring is begun under nitrogen flow. The mixture is refluxed for 3 hours at 95°-100° C. Water is added, and the crude product (17.3 9) is filtered and crystallized from xylene and then from chloroform. The final crystallization yields 14.5 g of an off-white solid, 83.8% recovery, m.p. 115°-119° C. 31P NMR shows a single peak of −4.0 ppm. $^1$H NMR shows proton resonances at 2.45 ppm., 4 protons, (2×SC$\underline{H}_2$); 2.82 ppm., 8 protons, (2×C$\underline{H}_2$C$\underline{H}_2$S); 4.30 ppm., 4 protons, (2×C$\underline{H}_2$—O—); OH is not specifically observed.

Analysis for $C_{25}H_{17}F_{34}O_4PS_2$: Calculated.. C, 26.6%; H, 1.6%., S, 5.7%, F, 57.2%; Found: C, 26.8% H, 1.4%, S, 5.9%; F, 57.1%.

Example 2

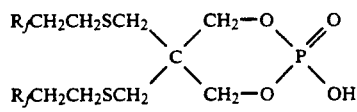

5,5-bis(1,1,2,2-tetrahydroperfluoroalkylthiomethyl)-2-hydroxy-2-oxo-1,3,2-dioxaphosphorinane where $R_f$ is $C_6F_{13}$—, $C_8F_{17}$—, $C_{10}F_{21}$—, $C_{12}F_{25}$—, $C_{14}F_{29}$— in the ratio of 36.8, 35.5, 18.4, 7.4, 1.9

2,2-Bis(1,1,2,2-tetrahydroperfluoroalkylthiomethyl)-1,3-propanediol (12.8 g, 0.012 mol) and polyphosphoric acid (5.16 g) are charged to a three-necked flask. Diethylene glycol dimethyl ether (4.0 g) is added as solvent, and the reaction mixture is heated to 100° C. for four hours with agitation under nitrogen. Water is added, and the product, a white solid, is isolated by vacuum filtration.

Examples 3a and 3b

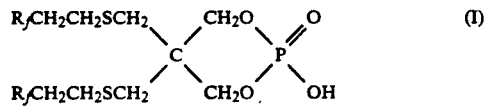 (I)

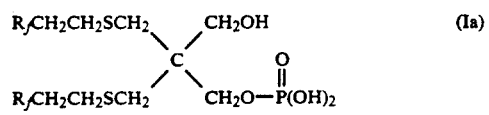 (Ia)

(I)

5,5-Bis(1,1,2,2-tetrahydroperfluoroalkylthiomethyl)-2-hydroxy-2-oxo-1,3,2-dioxaphosphorinane (Ia)

2,2-Bis(1,1,2,2-tetrahydroperfluoroalkylthiomethyl)-3-hydroxy-1-propyl Dihydrogenphosphate 2.2-Bis1,1,2,2-tetrahydroperfluoroalkylthiomethyl)-1,3-propanediol (12.8 g, 0.012 mol) and polyphosphoric acid (5.16 g) are charged to a three-necked flask. Diethylene glycol dimethyl ether (4.0 g) is added as solvent, and the reaction mixture is heated to 100° C. for four hours with agitation under nitrogen. In order to obtain structure (I), (Example 3a), water is added, and the product, a white solid, is isolated by vacuum filtration. To obtain structure (Ia) (Example 3b), water (40 g) is added, and the reaction mixture is heated at 100° C. for an additional six hours with agitation. The product, a white solid, is isolated by vacuum filtration and washed several times with water. Traces of (Ib), 2,2-bis(1,1,2,2-tetrahydroperfluoroalkylthiomethyl)-1,3-propanedihydrogenphosphate are usually present, as idicated by $^{31}$P NMR.

Analysis for structure (I) follows:

$^{31}$P NMR shows two major peaks for samples derivatized with N,O-bis-trimethylsilyl) trifluoroacetamide reagent: −30.0 ppm., 47 parts, the standard shift for phosphoric acid and −17.0 ppm., 53 parts, corresponding to structure (I). Additional proof for structure (I) comes from the addition of trichloroacetyl isocyanate (TCAI) reagent. Transformation of P—OH moiety into the more bulky P—O—TCAI ester results in freezing the spectrum from that of rapidly equilibrating chair conformations to that of a conformationally invariant species. This is most likely one in which the —O—TCAI moiety is equatorial. The resulting spectrum shows two $R_f$ moieties and a complex region for the ring —OCH$_2$ resonances in which the axial and equatorial protons are no longer equivalent, and show different couplings to phosphorus. $^1$H NMR shows proton resonances at 2.52 ppm., complex, 4 protons, $(2 \times R_f\underline{CH}_2)$ 2.82 ppm., triplet, 4 protons, $(2 \times CH_2\underline{CH}_2S)$; 2.82 ppm., singlet, 4 protons, $(2 \times \underline{CH}_2C)$; 4.29 ppm., doublet, 4 protons, $(2 \times \underline{CH}_2O)$; OH is not specifically observed.

Analysis for structure (Ia) follows:

$^{31}$P NMR contains three major peaks for samples derivatized with N,O-bis(trimethylsily)trifluoroacetamide: −19.2 ppm., 1 part, corresponding to structure (I) −22.2 ppm., 4 parts, corresponding to structure (Ia); and −30.3 ppm., 1 part, corresponding to phosphoric acid. Traces of Ib are usually present.

Example 4

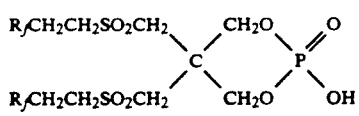

5,5-bis(1,1,2,2-tetrahydroperfluoroalkylsulfonylmethyl)-2-hydroxy-2-oxo-1,3,2-dioxaphosphorinane 5,5-Bis(1,1,2,2-tetrahydroperfluoroalkylsulfonylmethyl)-2-hydroxy-2-oxo-1,3,2-dioxaphosphorinane (36.0 g 0.032 mol) and acetic acid (48.0 g, 0.80 mol) are charged to a three-necked flask and heated to 40° C. Hydrogen peroxide (30%, 7.0 g is added, and the reaction mixture is agitated for one hour under nitrogen. Additional hydrogen peroxide (30%, 14.0 g) is added, and the mixture is heated to 100° C. for 4½ hours with agitation under nitrogen. The temperature is dropped to room temperature, and the crude product, a pale yellow solid, is isolated by vacuum filtration, washed several times with water and dried under high vacuum over Drierite and potassium hydroxide, yielding a white solid (30.1 g, 82% of theory), m.p. 285°-290° C. $^{31}$P NMR gives a major peak at −19.0 ppm. $^1$H NMR gives proton resonances at 2.90 ppm., complex, 4 protons, $(2 \times R_f\underline{CH}_2)$; 3.70 ppm., complex, 4 protons $(2 \times R_f\underline{CH}_2CH_2)$; 4.01 ppm., singlet, 4 protons, $((2 \times SO_2\underline{CH}_2)$; 4.65 ppm., doublet, 4 protons $(2 \times \underline{CH}_2O)$; OH is not specifically observed.

Example 5

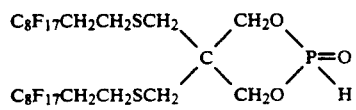

5,5-Bis(1,1,2,2-tetrahydroperfluorodecylthiomethyl)-2-hydro-2-oxo-1,3,2-dioxaphosphorinane 2,2-Bis(1,1,2,2-tetrahydroperfluorodecylthiomethyl)-1,3-propanediol (10.0 g, 0.0094 mol), diethyl phosphite (2.3 g, 0.014 mol) and sodium methoxide (25%, catalytic amount) are charged to a three-necked flask. The reaction mixture is heated to 140° C. for 4½ hours with agitation under nitrogen and then cooled to room temperature. The crude product is triturated with ether, isolated by vacuum filtration and dried under high vacuum, yielding a white solid (10.22 g, 97% of theory) m.p. 107°-110° C., 96% purity by GLC. $^{31}$P NMR shows a major peak at 3.5 ppm. $^1$H NMR shows proton resonances at 2.41 ppm., complex, 4 protons, $(2 \times C_8F_{17}\underline{CH}_2)$; 2.80 ppm., triplet, 4 protons $(2 \times CH_2\underline{CH}_2S)$; 2.82 ppm., singlet, 4 protons, $(2 \times S\underline{CH}_2C)$; 4.30 ppm., complex, 4 protons, $(2 \times \underline{CH}_2O)$.

Analysis for $C_{25}H_{17}F_{34}O_3PS_2$: Calculated: C, 27.0%; H, 1.5%; F, 58.1%, 442 Found: C, 26.9%., H, 1.5%, F, 56.9%.

Example 6

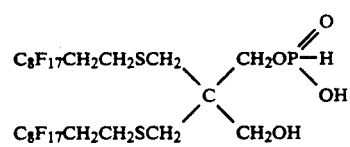

2,2-Bis(1,1,2,2-tetrahydroperfluorodecylthiomethyl)-3-hydroxy-1-propyl Hydrogen Phosphite Hydrolysis of the compound prepared in Example 5, 5,5-bis-(1,1,2,2-tetrahydroperfluorodecylthiomethyl)-2-hydro-2-oxo-1,3,2-dioxaphosphorinane, yields the monophosphite. $^1$H NMR of this gives proton resonances at 2.48 ppm., complex, 4 protons $(2 \times C_8F_{17}\underline{CH}_2)$; 2.70 ppm., singlet, 4 protons $(2 \times S\underline{CH}_2)$; 2.83 ppm., triplet, 4 protons, $(2 \times \underline{CH}_2S)$; 3.54 ppm., singlet, 2 protons, $(\underline{CH}_2OH)$; 3.7 ppm., doublet, 2 protons, $(\underline{CH}_2OP)$; OH is not specifically observed. Traces of 2,2-bis(1,1,2,2-tetrahydroperfluorodecylthiomethyl) -1,3-propanedihydrogen-phosphite are usually present.

Example 7

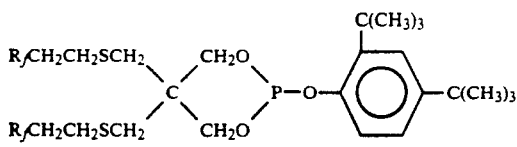

2-(2,4-di-tert-butylphenoxy)-5,5-bis-(1,1,2,2-tetrahydroperfluoroalkylthiomethyl)-1,3,2-dioxaphosphorinane 2,2-Bis(1,1,2,2-tetrahydroperfluoroalkylthiomethyl)-1,3-propanediol (53.0 g 0.05 mol), triphenyl phosphite (18.6 g, 0.06 mol), 2.4-di-tertbutylphenol (13.52 g, 0.07 mol) and sodium methoxide (25%, catalytic amount) are charged to a three-necked flask. The reaction mixture is heated to 140° C. with agitation for five hours under high vacuum to drive off phenol by-product. GLC still shows incomplete reaction. Thus, the temperature is raised to 195° C., and the reaction mixture is agitated for an additional 5 hours, when GLC shows 50% completion. Toluene is added and the reaction mixture is cooled to room temperature and vacuum filtered. The product is present in the filtrate (clear yellow liquid). For analytical purpose flash chromatography is performed on one-third of the filtrate (75 g) using a 95:5 hexane to ethyl acetate solvent system. This procedure yields 3.93 g of a white solid, m.p. 98°-99° C., 96% purity by GLC. A trace amount of triisopropanolamine is added to prevent decomposition. $^1$H NMR shows proton resonances at 1.32 ppm., singlet, 9 protons [p-C(CH$_3$)$_3$]; 2.40 ppm., complex, 4 protons, (2×R$_f$CH$_2$); 2.48 ppm., singlet, 2 protons (2×SCH$_2$ axial); 2.75 ppm., complex, 2 protons, (2×SCH$_2$ equatorial); 3.84 ppm., triplet, 2 protons, (2×CCH$_2$O equatorial); 4.48 ppm., complex, 2 protons, (2×CCH$_2$O axial); 6.98 ppm., doublet, 1 proton, (POCCH); 7.18 ppm. complex, 1 proton, [C(CH$_3$)$_3$CHC(CH$_3$)$_3$]; 7.40 ppm., doublet, 1 proton (POCCHCH).

Analysis for C$_{39}$H$_{37}$F$_{34}$O$_3$PS$_2$: Calculated: C, 36.1%; H, 2.9%., F, 49.6%; Found: C, 35.9%., H, 2.5%, F, 49.7%.

Examples 8 to 14

Using the methods described and by techniques similar to Examples 1 to 6, the following additional phosphates/phosphites where X is —S—, —SO$_2$—, —O—, —NR—, —CONH—, and SO$_2$NR— are prepared.

| Ex. | Perfluoroalkl Glycol | Phosphate/Phosphite (Type) |
|---|---|---|
| 8 | (CF$_3$CF$_2$CH$_2$SCH$_2$)$_2$C(CH$_2$OH)$_2$ | I |
| 9 | (C$_6$F$_{13}$(CH$_2$)$_4$SO$_2$CH$_2$)$_2$C(CH$_2$OH)$_2$ | II |
| 10 | (C$_8$F$_{17}$CH$_2$CH$_2$OCH$_2$)$_2$C(CH$_2$OH)$_2$ | Ia |
| 11 | (C$_8$F$_{17}$CH$_2$CH$_2$N(CH$_3$)CH$_2$CH$_2$SCH$_2$)$_2$C(CH$_2$OH)$_2$ | Ia |
| 12 | (C$_8$F$_{17}$SO$_2$NHCH$_2$CH$_2$OCH$_2$)$_2$(CH$_2$OH)$_2$ | Ib |
| 13 | (C$_8$F$_{17}$CH$_2$CH$_2$SO$_2$NHCH$_2$CH$_2$SCH$_2$)$_2$C(CH$_2$OH)$_2$ | IIa |
| 14 | (C$_7$F$_{15}$CONHCH$_2$CH$_2$SCH$_2$)$_2$C(CH$_2$OH)$_2$ | II |

Example 15

This example describes comparative internal size performance evaluations of the subject 5,5-bis(perfluoroalkylthiomethyl)-2-hydroxy-2-oxy -1,3,2-dioxaphosphorinane, triethanolammonium salts, Examples 2 and 3a versus a commercial phosphate size SCOTCHBAN FC-807 (3M), a bis-perfluoroalkyl phosphate ester, ammonium salt. The subject phosphoric acids are prepared in water as triethanolamine salts with an excess of triethanolamine.

The results indicate equivalent performance.

| | | Hold-out Tests | |
|---|---|---|---|
| Fluorine on Wt. of Paper | Oil Kit Number | Hot, 110° C. Corn Oil | Hot, 80° C. Water + 0.5% TRITON X-165 |
| Compound of | | | |
| Ex. 2  0.05 | 4 | >20 min. | >20 min. |
| Ex. 3a  0.05 | 4 | >20 min. | >20 min. |
| FC-807  0.05 | 4 | >20 min. | >20 min. |

Example 16

This example describes comparative external size performance of the subject 5,5-bis(1,1,2,2-tetrahydroperfluoroalkylthio-methyl)-2-hydroxy-2-oxo-1,3,2-dioxaphosphorinane, (Example 3a); its mixture with the acyclic acid ester, 2,2-bis(1,1,2,2-tetrahydroperfluoroalkylthiomethyl)-3-hydroxy -1-propyl dihydrogen phosphate (Example 3b), both as triethanolammonium salts, and SCOTCHBAN FC-807 (3M). The products are applied to paper by pad application and tested for Oil Kit Rating and the Grease Resistance Test.

The results show that the subject phosphates have superior performance at much lower application levels. Further, the novel phosphates have the potential to pass the Grease Resistance Test at lower Kit Numbers. This allows their application to products requiring better adhesive bonding, better label adhesion, and lessened problems with printing.

| % Fluorine on Wt. of Paper | Oil Kit Number | Grease Resistance Test |
|---|---|---|
| Compound of | | |
| Ex. 3a  0.045 | 7 | pass |
| Ex. 3b  0.045 | 5 | pass |
| FC-807  0.065 | 6-7 | pass |

What is claimed is:

1. A compound of formula Ia, Ib, IIa or IIb:

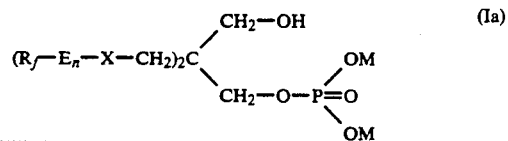

(Ia)

-continued

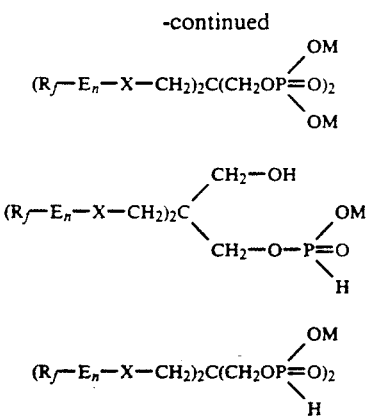

wherein $R_f$ is a straight or branched chain perfluoroalkyl of 2 to 12 carbon atoms or perfluoroalkyl of 2 to 6 carbon atoms substituted by perfluoroalkoxy of 2 to 6 carbon atoms, $n = 1$ or $0$, and when $n = 1$, E is a branched or straight chain alkylene of 2 to 10 carbon atoms or said alkylene interrupted by one to three groups selected from the group consisting of —NR—, —O—, —S—, SO$_2$—, —CONR—, —NRCO—, —SO$_2$NR—, and —NRSO$_2$—, or terminated at the $R_f$ end with —CONR— or —SO$_2$NR—, where $R_f$ is attached to the carbon or sulfur atom, and X is —S—, —O—, or —SO$_2$—and when $n=0$, X is —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms, and M is independently hydrogen, lower alkyl, an alkyl- or mixed polyalkyl- substituted aromatic group, or represents an ammonium, organoammonium, alkali metal or alkaline earth metal salt of the respective phosphite or phosphate group.

2. A compound of formula Ia, Ib, IIa or IIb, according to claim 1 wherein $R_f$ is a straight or branched chain perfluoroalkyl of 2 to 12 carbon atoms.

3. A compound of formula Ia, Ib, IIa, or IIb according to claim 1 wherein $R_f$ is a straight or branched chain perfluoroalkyl of 2 to 12 carbon atoms, and E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$—, —CH$_2$CH$_2$OCH$_2$CH$_2$—, or —SO$_2$NHCH$_2$CH$_2$—.

4. A compound of formula Ia, Ib, IIa, or IIb according to claim 1 wherein $R_f$ is perfluoroalkyl of 6 to 12 carbon atoms, E is ethylene, X is —S—.

5. A compound according to claim 1 which is 2,2-bis(1,1,2,2-tetrahydroperfluoroalkylthiomethyl)-3-hydroxy-1-propyl dihydrogen phosphate.

6. A compound according to claim 1 which is 2,2-bis(1,1,2,2-tetrahydroperfluoroalkylthiomethyl)-1,3-propanedihydrogen phosphate.

7. A compound according to claim 1 which is 2,2-bis(1,1,2,2-tetra-hydroperfluorodecylthiomethyl)-3-hydroxy-1-propyl hydrogen phosphite.

8. A compound according to claim 1 which is 2,2-bis(1,1,2,2-tetra-hydroperfluorodecylthiomethyl)-1,3-propanedihydrogenphosphite.

9. A compound according to claim 1 wherein M is ammonium or organoammonium.

10. A compound according to claim 2 wherein M is ammonium or organoammonium.

11. A compound according to claim 3 wherein M is ammonium or organoammonium.

12. A compound according to claim 4 wherein M is ammonium or organoammonium.

13. An ammonium or organoammonium salt of the compound according to claim 5.

14. An ammonium or organoammonium salt of the compound according to claim 6.

15. An ammonium or organoammonium salt of the compound according to claim 7.

16. An ammonium or organoammonium salt of the compound according to claim 8.

* * * * *